United States Patent [19]

Nicolotti et al.

[11] Patent Number: 4,732,974
[45] Date of Patent: Mar. 22, 1988

[54] METAL ION LABELING OF CARRIER MOLECULES

[75] Inventor: Robert A. Nicolotti, Furguson; Alan R. Ketring, Ashland, both of Mo.; Koon Y. Pak, Frazer, Pa.

[73] Assignee: Mallinckrodt, Inc., St. Louis, Mo.

[21] Appl. No.: 836,535

[22] Filed: Mar. 5, 1986

[51] Int. Cl.$^4$ .................. C07K 3/08; A61K 39/00; A61K 39/42; A61K 43/00
[52] U.S. Cl. .................. 530/390; 204/131; 204/180.1; 424/1.1; 424/85; 436/512; 436/547; 436/548; 530/345; 530/388; 530/400
[58] Field of Search .............. 530/388, 345, 390, 400; 424/1.1, 85; 436/512, 547, 548; 204/131, 180.1

[56] References Cited

U.S. PATENT DOCUMENTS

| | | | |
|---|---|---|---|
| 4,331,647 | 5/1982 | Goldenberg | 424/1.1 |
| 4,421,735 | 12/1983 | Haber et al. | 424/1.1 |
| 4,472,509 | 9/1984 | Ganson et al. | 424/1.1 X |
| 4,474,690 | 10/1984 | Nylen | 530/413 |
| 4,569,794 | 2/1986 | Smith et al. | 530/415 X |
| 4,592,998 | 6/1986 | Avrameas et al. | 435/188 X |

FOREIGN PATENT DOCUMENTS

| | | |
|---|---|---|
| 0083129 | 6/1983 | European Pat. Off. |
| 2109407 | 6/1983 | United Kingdom |

OTHER PUBLICATIONS

*J. Inorg. Chem.*, 30:3107–3109 (1968).
P. Letkeman et al., *J. Coord. Chem.*, 10:47–53 (1980).
M. A. Bassinger et al., *Res. Comm. in Chem. Path. and Pharm.*, 36:519–522 (1982).
M. A. Basinger et al., *Res. Comm. in Chem. Path. and Pharm.*, 34:351–358 (1981).
Moerlein et al., *J. Nucl. Med. Biol.*, vol. K, pp. 277–287 (1981).
*Catecholate Complexes of $^{99m}Tc$*, "Technetium in Chemistry and Nuclear Medicine", eds. E. Deutsch et al., Cortina International (1983).
*Complexometric Titrations*, Methuen & Co., Ltd., London (1969).

*Primary Examiner*—Howard E. Schain
*Attorney, Agent, or Firm*—Bernard, Rothwell & Brown

[57] ABSTRACT

A conjugate of a protein or polypeptide and a metal ion is prepared by reacting a metal ion transfer complex comprising a chelate of 4,5-dihydroxyl-m-benzenedisulfonic acid or a salt thereof with a protein or polypeptide that is covalently bound to an exogenous chelating group having a greater affinity than 4,5-dihydroxyl-m-benzenedisulfonic acid for the metal ion.

11 Claims, 2 Drawing Figures

| REACTION MIXTURE | % OF TOTAL COUNTS IN PROTEIN PEAK | |
|---|---|---|
| TcO₄⁻(89.5%) + Tiron before electrolytic reduction | --- |  |
| Tiron-Complex (89.2%) after electrolytic reduction | --- |  |
| F(ab')₂ -MAG₃ + Tiron Complex | 86.3 |  |
| F(ab')₂ -CO₂DADS + Tiron Complex | 88.2 |  |
| F(ab')₂ -acetyl + Tiron Complex | 6.0 |  |

METAL ION LABELING OF CARRIER MOLECULES

BACKGROUND OF THE INVENTION

Metal ions are very useful as reporter substances. They can be detected in very low concentrations by emission of radioactivity, fluorescence, electron spin resonance and NMR relaxation. When attached to a carrier molecule, such as an antibody or an antigen, they can report its concentration or location. The carrier molecule may have an avidity for disease associated molecules, e.g., tumor-associated antigens. Thus, carrier molecules conjugated to metal ions can be used as in vivo and in vitro diagnostic tools to detect the presence and/or location of disease in the body. Certain radiation-emitting metal ions may also be attached to carrier molecules, such as antibodies to tumor cell surface antigens, for the purpose of carrying the metal ions to a tumor site in order to irradiate the tumor.

Problems may be encountered when attempting to label certain carrier molecules with some metal ions. Conditions which stabilize the metal ion may not be compatible with stability of the carrier molecule and vice versa. An example of such incompatibility occurs in the labeling of a protein or polypeptide with indium-111 or gallium-67. Metal ions can be joined to a protein or polypeptide by producing a derivative of the protein or polypeptide which contains a moiety having a terminal chelating group capable of forming a chelate with the metal ion. For example, my copending U.S. patent application Ser. No. 650,127 describes a method of joining a radionuclide metal ion to an antibody fragment using a bifunctional coupling agent which reacts with a free sulfhydryl group of the antibody fragment and also contains a chelating group capable of complexing a metal ion. U.K. Patent Application GB No. 2 109 407 also describes the use of chelate-derivatized antibodies to form antibody-metal ion conjugates for use in tumor imaging. When labeling chelate-derivatized proteins with indium-111 or gallium-67 two problems are encountered. These metal ions are used in the form of their chloride salts, which must be kept in aqueous solutions at a pH less than 3.5. If they are not, they will react with water to form insoluble metal hydroxides. This acidic pH may adversely affect the stability or biological activity of the protein or polypeptide.

Technetium presents an additional set of problems for protein labeling. Technetium exists in 7 oxidation states, the most stable one being +7 as in pertechnetate ($TcO_4^-$). The +5 state is very useful for labeling chelates and chelate coupled proteins. However, this oxidation state is not easily achieved. Being metastable, technetium (+5) is easily reduced to (+4), and trapped as reduced-hydrolyzed $TcO_2$ in the presence of excess reducing agent. Reduced-hydrolyzed technetium is not useful for chelate or protein labeling, because of its tendency to self-associate or bind non-specifically to surfaces. If stoichiometric amounts of reducing agents are used, reduction is kinetically very inefficient. The +5 technetium so generated has a tendency to reoxidize to pertechnetate as soon as the reducing agent is consumed.

Other problems are encountered in forming chelate complexes because of functional groups on the protein or polypeptide molecules. The amino and carboxyl terminus, the amide bond backbone and the side chain residues of aspartic and glutamic acid, lysine, cysteine, tyrosine and histidine found in proteins and polypeptides all possess chelate ligand character. The amino acid sequence and tertiary structure of the molecule can bring these chelate ligands together to create strong, multidentate metal ion binding sites. Thus, each protein possesses a spectrum of metal binding properties. The weak sites can leach the metal ion in the blood stream to other plasma proteins or small molecular weight constituents. The strong sites interfere with protein metabolism. This invariably leads to radionuclide retention in major protein catabolic sites such as the liver and kidney.

One particularly troublesome problem encountered with technetium labeling of antibodies during in situ reduction of pertechnetate is the concomitant reduction of protein disulfide bonds. The resulting sulfhydryl groups bind technetium in preference to coupled chelates (Paik, C.H. et al., *J. Nucl. Med. Biol.*, 12:3 [1985]). The resulting labeled antibody yields metabolites that do not clear from liver or kidney. This is an ideal property for technetium labeled microaggregated albumin for imaging normal liver, but it is highly undesirable for labeled antibodies used for in vivo diagnostic applications, where clearance of the radionuclide from the liver is desired.

The magnitude of this clearance problem can be appreciated if one considers the metabolic fate of labeled antibodies. A consistent observation in the use of labeled antibodies for tumor detection is that only a small fraction of the injected dose goes to the target solid tumor (Larson, S.M., et al., *J. Clin. Invest.*, 72:2101-2114 (1983); Buraggi, G.L., et al., *Cancer Res.*, 45:3378-3387 (1985); Reviewed in: Halpern, S.E., et al., *Diagnostic Imaging*, June, 40–47 (1983)). This is because the tumor has a relatively low blood flow and vascular permeability. Thus, the tumor has a very low labeled antibody extraction efficiency in comparison to competing catabolic pathways of labeled antibody uptake. Under optimal conditions, a target tissue will take up from 3–10% of the injected dose. More often, tumor uptake is less than 1%. The remainder, 90% or more, must be processed by the liver and kidneys. Antibodies labeled with radionuclide metal ions by procedures of the prior art do not provide rapid washout of the radiolabeled catabolites from these sites. There are two adverse consequences of this radionuclide retention. The high level of radiation being emitted from the liver or kidneys obscures the low level of radiation coming from the target tumor. More importantly, the liver and kidneys, being among the most radiosensitive organs, accumulate an unacceptable dose of radiation. Dosimetry is linearly dependent on label concentration, but exponentially dependent on time of exposure. Therefore, decreasing the liver and kidney exposure time from no clearance to a fraction of the radionuclide's half-life will yield a dramatic decrease in radiation dose.

It would be highly desirable to devise an antibody labeling method that causes a radionuclide to be retained on the surface of the target tumor cells for at least two half-lives, but yields labeled metabolites which have biological half-lives of less than 60 minutes in normal clearance organs.

One method of labeling a chelate-derivatized protein or polypeptide, such as an antibody, involves the use of a so-called "transfer ligand." A transfer ligand is a compound which forms an intermediate complex with the metal ion. The metal ion complex with the transfer ligand is soluble under conditions in which the protein is stable. The complex between the transfer ligand and the metal ion is such that the metal ion is transferred upon contact with the chelate-derivatized protein which has a stronger chelating affinity for the metal ion than does the transfer ligand. European Patent Application No. 82201602.8 describes a method of labeling proteins with radionuclide metal ions which employs an intermediate complex of the metal ion in the form of a carboxylate, dithiocarboxylate, enolate or mixture thereof.

For various reasons, the transfer ligands employed in the prior art have not been completely satisfactory. Ideally, a transfer ligand possesses a unique profile of properties. For use in conjunction with radionuclides having stable oxidation states, such as indium-111 and gallium-67, these properties are as follows:

1. It prevents the radionuclide metal ion from forming metal hydroxides in physiologic buffers at neutral pH;
2. It prevents the radionuclide metal ion from binding to moderately strong endogenous chelating ligands of native or chelate-derivatized proteins;
3. It transfers the radionuclide metal ion rapidly and quantitatively to strong chelating groups that have been coupled to the protein;
4. It is water soluble, non-toxic and non-mutagenic; and
5. It is readily available and, preferably, inexpensive.

For use in conjunction with oxidation-sensitive radionuclides, such as technetium, the transfer ligand should also possess the following properties:

6. It quantitatively traps the radionuclide metal ion in the proper oxidation state during the reduction process for subsequent chelation; and
7. It prevents the reoxidation of the radionuclide metal ion when the reducing agent is removed.

To meet these criteria, a transfer ligand must possess two physicochemical properties. Its complex with the radionuclide ion must be kinetically labile, permitting rapid exchange when it is presented with a more thermodynamically stable multidentate ligand. Additionally, the transfer ligand must have sufficient thermodynamic stability to prevent exchange with hydroxide ions or endogenous chelating sites on protein molecules in aqueous buffers at physiologic pH. While the former property is generally characteristic of metal ion indicators used in ethylenediaminetetraacetic acid complexometric titrations, very few of the metal ion indicators or the weak chelating agents (such as those described in European Patent Application No. 82201602.8) meets all seven of the criteria listed above for an ideal transfer ligand.

SUMMARY OF THE INVENTION

This invention provides methods for the preparation of conjugates of proteins or polypeptides with metal ions. The conjugates prepared by the methods of the invention are useful as reporter substances for in vivo and in vitro diagnostic applications and, in the case of certain radionuclide metal ions, for targeted delivery as therapeutic agents. In accordance with the method of the invention, a metal ion transfer complex comprising a chelate of 4,5-dihydroxyl-m-benzenedisulfonic acid or a salt thereof and a metal ion is reacted with a protein or polypeptide that is covalently bound to an exogenous chelating group. The exogenous chelating group has a greater chelating affinity than does 4,5-dihydroxyl-m-benzenedisulfonic acid for the metal ion. The reaction is carried out in an aqueous medium at a pH at which the protein or polypeptide is stable. I have found that 4,5-dihydroxyl-m-benzenedisulfonic acid (also known as "tiron") is an ideal transfer ligand for joining metal ions to chelate-derivatized proteins or polypeptides inasmuch as it fulfills the seven requirements set forth above.

In one embodiment of the invention, there is provided a method for preparing a conjugate of a protein or polypeptide and a technetium ion, e.g., Tc-99m in which the technetium ion is in a reduced state, i.e., less than +7. In accordance with this embodiment, 4,5-dihydroxyl-m-benzenedisulfonic acid and pertechnetate ions are reacted in an aqueous reaction medium and the pertechnetate ion is electrolytically reduced in the aqueous medium, thus producing a transfer complex having the technetium ion in a reduced state. The transfer complex is reacted with a protein or polypeptide that is covalently bound to an exogenous chelating group, the exogenous chelating group having a greater chelating affinity than 4,5-dihydroxyl-m-benzenedisulfonic acid for the reduced technetium ion. The reaction is carried out in aqueous reaction medium at a pH at which the protein or polypeptide is stable. The 4,5-dihydroxyl-m-benzenedisulfonic acid traps the technetium in the reduced oxidation state and prevents reoxidation when the reducing agent is removed.

DETAILED DESCRIPTION AND PREFERRED EMBODIMENTS

Figure 1:
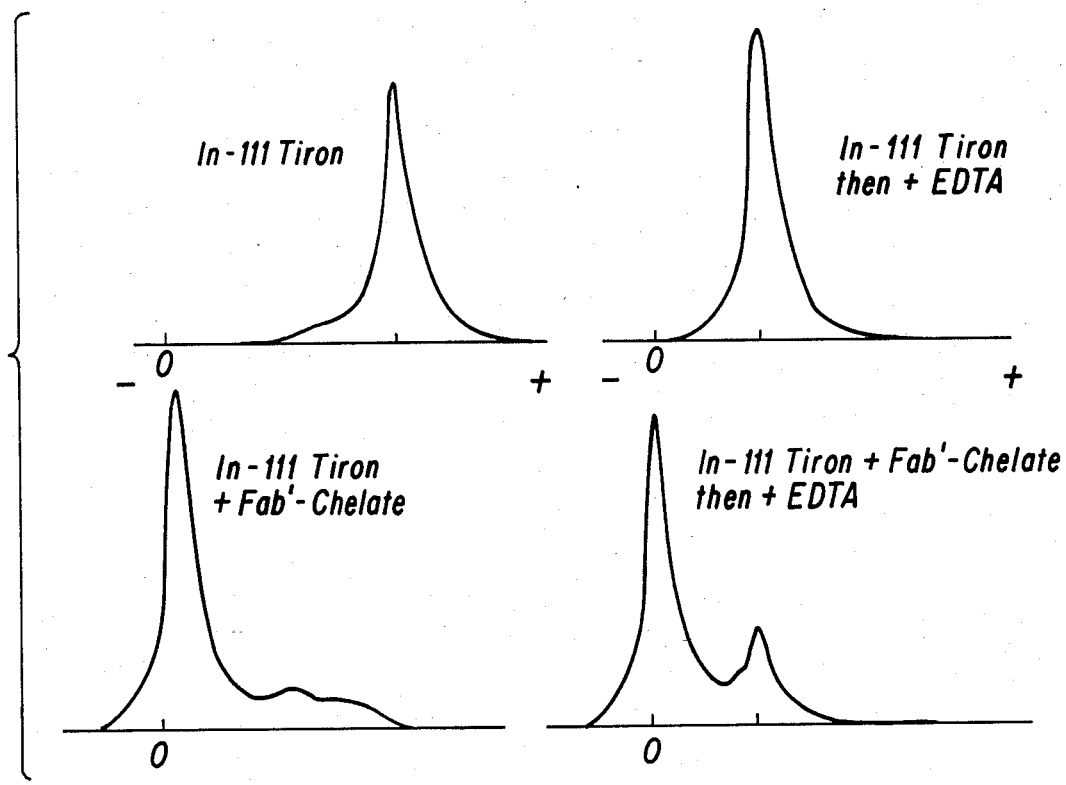
FIG. 1 presents the results of electrophoresis of a tiron-$^{111}$In complex and a tiron-$^{111}$In-antibody complex before and after being challenged with EDTA.

This invention provides methods for the preparation of conjugates of proteins or polypeptides with metal ions. The resulting conjugates are useful as radiopharmaceuticals. The invention is based on the discovery that 4,5-dihydroxyl-m-benzenedisulfonic acid, i.e., tiron, is an ideal transfer ligand for producing such conjugates. Chelates of tiron are known per se. Tiron has been used as a chelating agent, for example, in complexometric titrations of metal ions such as $Al^{3+}$, $Ga^{3+}$ and $In^{3+}$. Also, tiron has been used as an antidote, alone or in combination with other chelates, for the treatment of iron overload, lead, antimony and acute uranium intoxication (Basinger, M. A. and Jones, M. M., *Res. Comm. in Chem. Path. and Pharm.*, 34:351 [1981]). More recently, the Tc-99m complex of tiron has been shown to have efficacy as a kidney imaging agent (*Cathecholate Complexes of 99mTc in Technetium Chemistry and Nuclear Medicine*, eds. Deutsch, E., Nicolini, M. and Wagner, H. N., p. 113, Raven Press [1983]). There have been no reports, however, of the use of tiron as a transfer ligand in the preparation of radiopharmaceuticals such as those described herein.

One can employ the methods of the invention to produce conjugates of metal ions with any protein or polypeptide that it is desired to label. While the invention will be described hereafter with respect to its use in conjunction with proteins, it is to be understood that the methods of the invention are also applicable to polypeptides or free chelates. The proteins which can be conjugated include antigens, antibodies and any other proteins which are useful for in vitro or in vivo diagnostic and therapeutic applications when joined to metal ions. Fragments of proteins may also be employed. In one embodiment of the invention, the protein employed is an antibody, an F(ab')₂ or an Fab' fragment thereof.

The protein which is conjugated with the metal ion by the method of the invention is first modified by covalently binding it to an exogenous chelating group. By "exogenous chelating group" is meant a chelating group which is not normally present on the protein molecule. The exogenous chelating group must have a greater chelating affinity than does tiron for the metal ion. Multidentate ligands having thermodynamic stability greater than tiron, and in the case of technetium labeling, all ligands containing one or more sulfhydryl groups, can be employed.

Any of a number of multidentate chelating groups may be suitably employed to modify the protein. The exogenous chelating group can be covalently bound to the protein molecule through any organic linker moiety which is reactive with a side chain of one or more amino acid residues in the protein molecule.

Copending U.S. patent application Ser. No. 650,127 describes the preparation of modified antibody fragments by reacting an Fab' fragment of an antibody having a free sulfhydryl group with a coupling agent of the formula

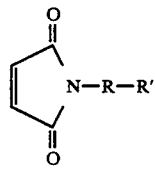

(I)

wherein R is a divalent organic radical, such as alkylene (C₁₋₂₀) or phenylene, which serves to join the maleimide moiety to the R' group and R' is a chelating group. Upon reacting the coupling agent with the antibody fragment, one obtains a modified antibody fragment of the formula

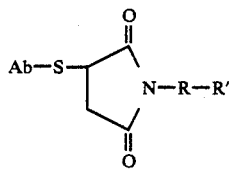

(II)

wherein R and R' are as described above and Ab is the residue of the antibody Fab' fragment. Coupling agents of formula I can be used to covalently bind a chelating group to any protein or fragment thereof having a cysteine side chain, i.e., a free sulfhydryl group. Exemplary coupling agents of formula I which can be used to modify proteins so that they can be employed in the method of the invention include

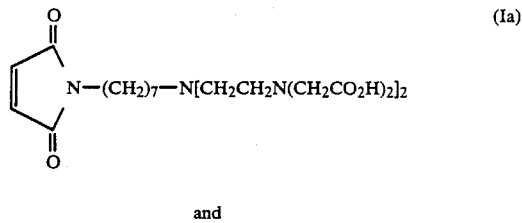

(Ia)

and

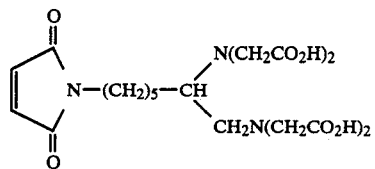

(Ib)

Compounds of the formula Ia and analogous compounds can be prepared in accordance with the following reaction scheme:

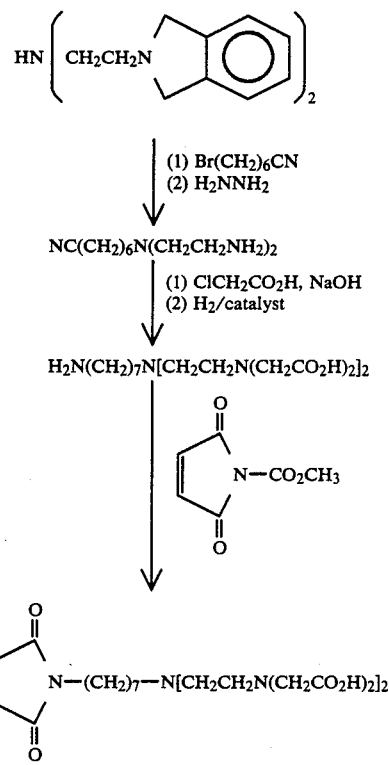

Compounds of formula Ib and analogous compounds can be prepared in accordance with the following reaction scheme:

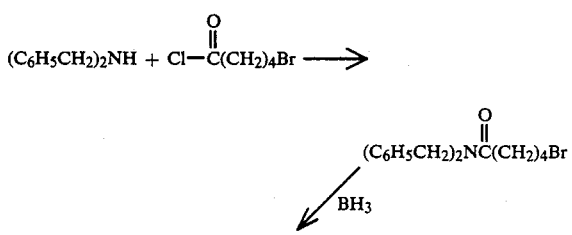

-continued (C6H5CH2)2N(CH2)5Br (1) Na+AcNHC−(CO2C2H5)2
    (2) H3O+
↓

(C2H5CH2)2N(CH2)5CHCO2H
                    |
                      NH2

(1) H+, CH3OH
    (2) NH3
↓

(C6H5CH2)2N(CH2)5CHCONH2
                    |
                      NH2

BH3 ↓

(C6H5CH2)2N(CH2)5CHCH2NH2
                  |
                  NH2

ClCH2CO2H, NaOH ↓

(C6H5CH2)2N(CH2)5CHCH2N(CH2CO2H)2
                  |
                  N(CH2CO2H)2

H2/catalyst ↓

H2N(CH2)5CHCH2N(CH2CO2H)2
          |
          N(CH2CO2H)2

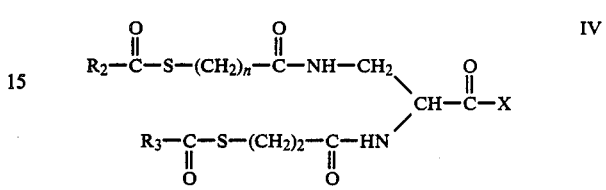

↓

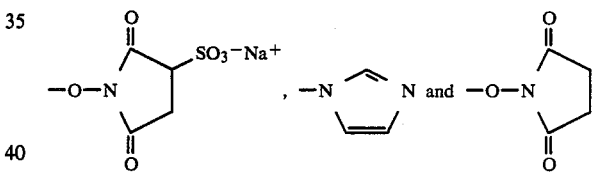

Other suitable coupling agents which can be used to modify proteins in order to covalently bind chelating agents thereto and which are preferably used when one desires to label the protein with a technetium ion, e.g. Tc-99m, they can be described by the general formulas:

$$R_1-\overset{O}{\underset{\|}{C}}-S-(CH_2)_n-\overset{O}{\underset{\|}{C}}-(AA)_i-\overset{O}{\underset{\|}{C}}-X \qquad III$$

or

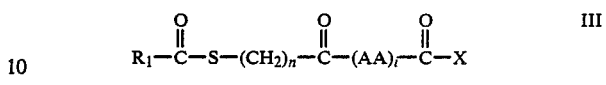

wherein $R_1$, $R_2$, and $R_3$ are the same or different and each represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, alkoxy, carboxy or sulfonate groups; n is either 1 or 2; AA are independently α or β amino acid residues linked to each other by amide bonds; i is an integer of from 2 to 6; and X is an activating group capable of forming an amide bond with an ε-amino group of the protein or polypeptide. Preferably, X is a member selected from the group consisting of a halogen, sodium sulfosuccinimidoyl, $N_3$,

[structures: sulfosuccinimidoyl-O-N, imidazolyl -N⌐N, and -O-N-succinimidyl]

the following are exemplary of coupling agents of formula III which can be employed to modify a protein to covalently bind a chelating agent to the protein:

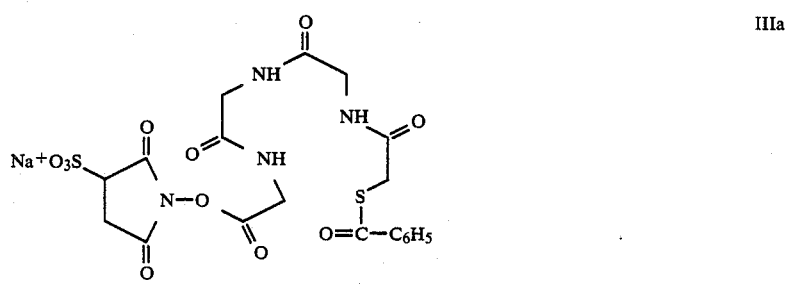

IIIa

-continued

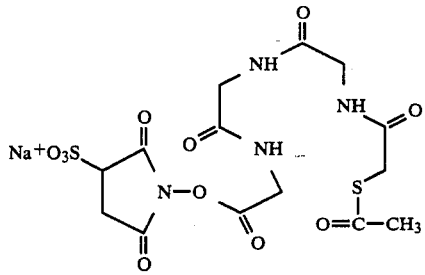
IIIb

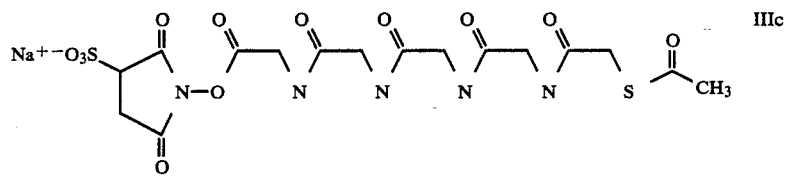
IIIc the following are exemplary of coupling agents of the formula IV which can be employed to attach the radionuclide metal ion to the ε-amino group of the antibody.

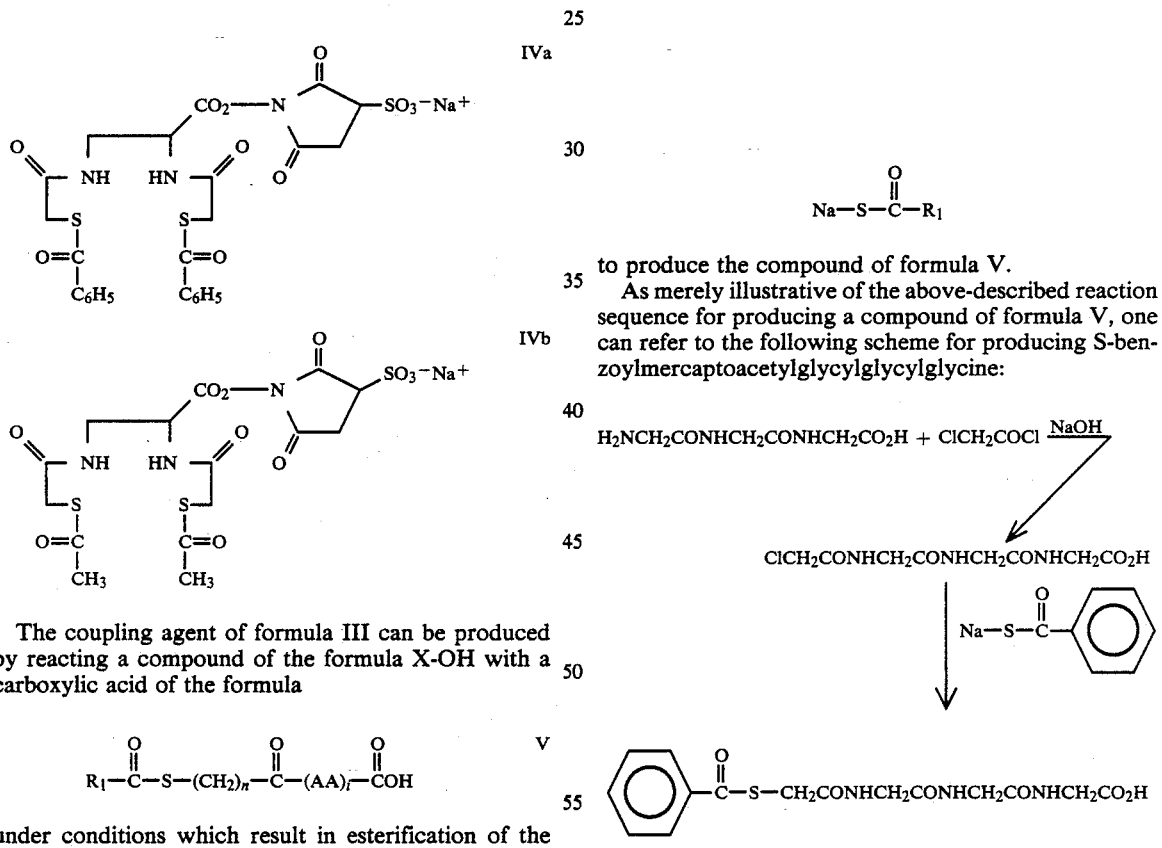

The coupling agent of formula III can be produced by reacting a compound of the formula X-OH with a carboxylic acid of the formula

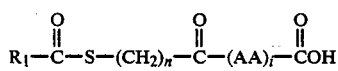
V under conditions which result in esterification of the carboxyl group. The compound of formula V, in turn, can be prepared from the polypeptide H-(AA)$_i$-CO$_2$H. The polypeptide is reacted with a chloroacylchloride, e.g., chloroacetylchloride, to produce a compound of the formula

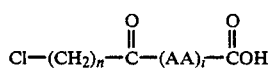
VI

The compound of formula VI can then be reacted with a compound of the formula $$Na-S-\overset{O}{\underset{\|}{C}}-R_1$$

to produce the compound of formula V.

As merely illustrative of the above-described reaction sequence for producing a compound of formula V, one can refer to the following scheme for producing S-benzoylmercaptoacetylglycylglycylglycine:

H$_2$NCH$_2$CONHCH$_2$CONHCH$_2$CO$_2$H + ClCH$_2$COCl $\xrightarrow{\text{NaOH}}$ ClCH$_2$CONHCH$_2$CONHCH$_2$CONHCH$_2$CO$_2$H $\downarrow$ Na—S—C(=O)—C$_6$H$_5$

C$_6$H$_5$—C(=O)—S—CH$_2$CONHCH$_2$CONHCH$_2$CONHCH$_2$CO$_2$H

The S-benzoylmercaptoacetylglycylglycylglycinate can then be reacted, for example, with sodium N-hydroxysulfosuccinimide to produce a compound of formula III, i.e., sodium sulfosuccinimidoyl(S-benzoylmercaptoacetylglycylglycylglycine). An analogous reaction scheme, using sodium thioacetate in place of sodium thiobenzoate, produces sodium sulfosuccinimidoyl (S-acetylmercaptoglycylglycylglycinate). The coupling agents of formula IV can be produced by reacting a compound of the formula X-OH with a carboxylic acid of the formula

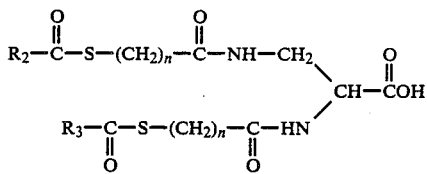

The preparation of a carboxylic acid of formula VII is illustrated by the following exemplary reaction scheme:

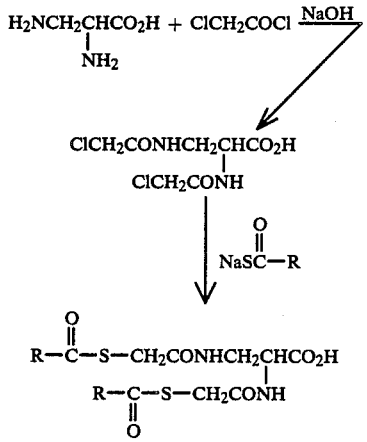

A coupling agent of formula III or IV can be reacted with an ε-amino side chain of any protein, such as an antibody or fragment thereof, to produce a chelate-modified protein useful in method of this invention.

Still other methods of modifying proteins by introducing exogenous chelating groups via covalent bonding are described in published U.K. Patent Application GB No. 2 109 407, the disclosure of which is incorporated herein by reference.

The coupling agents described above are merely illustrative of those which can be used to bond exogenous chelating groups to proteins in order to produce modified proteins useful in the practice of this invention. However, any protein containing a covalently bound exogenous chelating group can be employed, provided only that the exogenous chelating group has a stronger affinity than tiron for the metal ion.

The metal ion with which the protein can be conjugated by the method of this invention can be selected from the group consisting of Mg, Al, Ca, Sc, Ti V, Cr, Mn, Fe, Co, Ni, Cu, Zn, Ga, Sr, Y, Zr, Mo, Tc, Pd, Cd, In, Sn, Sb, Ba, Hf, W, Re, Hg, Tl, Pb, Bi, La, Ce, Rh, Pr, Nd, Sm, Eu, Gd, Tb, Dy, Ho, Er, Tm, Yd, Th, U, Pu and isotopes thereof.

The particular metal ion used will depend upon the desired end use of metal ion/protein conjugate. Radioisotopes of various metals are useful in diagnostic and therapeutic applications. For example, gamma-emitting radionuclide metal ions such as indium-III, gallium-67 and technetium-99m are preferred when the resulting conjugate is to be used in diagnostic scintigraphy for tumor detection. Beta-emitting isotopes, such as rhenium-186, rhenium-188, rhenium-189, rhodium-105, samarium-153, yttrium-90 and copper-67 are preferred when the conjugate is to be used therapeutically in the treatment of tumors.

When the conjugate is to be employed for in vivo detection or treatment of tumors, the protein employed will usually be an antibody (or fragment thereof) to one of the antigens which are known to be tumor markers such as carcinoembryonic antigen (CEA), alpha-fetoprotein, human chorionic gonadotropin or its beta sub-unit, colon specific antigen-p, tumor specific glycoprotein and the like.

In the method of the invention, the chelate-derivatized protein is reacted with a metal ion transfer complex comprising tiron and the metal ion. The transfer complex is formed by reacting tiron, usually in the form of its disodium salt, with the metal ion in an aqueous medium under conditions in which the metal ions are known to be stable in solution, i.e., they do not precipitate from solution as their hydroxides. For indium-111 and gallium-67, for example, the chloride salt of the metal is reacted in an aqueous medium at pH <3.5.

The reaction between the protein which is covalently bound to the exogenous chelating agent and the metal ion transfer complex is carried out in an aqueous reaction medium at a pH at which the protein is stable. By "stable" is meant that the protein remains soluble and retains its biological activity. Normally, the preferred pH for the reaction will be physiological pH, i.e., from about 5 to 8. The metal ion transfer complex and the protein are incubated, preferably at a temperature from about 20° C. to about 60° C., most preferably from about 20° C. to about 37° C., for a sufficient amount of time to allow transfer of the metal ion from the tiron to the exogenous chelating group on the protein. Generally, the reaction time of less than one hour is sufficient to complete the reaction. The metal ion labeled protein can be recovered by conventional protein recovery techniques such as high pressure liquid chromotography.

In the case of Tc-99m, it is advantageous to carry out an electrolytic reduction of the metal ion concomitantly with the formation of the metal ion transfer complex. Technetium is known to exist in 7 oxidation states, the most stable being +7, as in pertechnetate ($TcO_4^-$) The +5 state is very useful for labeing chelate-derivatized proteins to be used in diagnostic scintigraphy. However, $Tc^{+5}$ is metastable and easily reduced to $Tc^{+4}$ and trapped as reduced-hydrolyzed $TcO_2$ in the presence of excess reducing agent. Reduced-hydrolyzed technetium is not useful for protein labeling because of its tendency to self-associate or bind non-specifically to surfaces. If stoichiometric amounts of reducing agents are used, reduction is kinetically very inefficient. The $Tc^{+5}$ so generated has a tendency to reoxidize to pertechnetate as soon as the reducing agent is consumed.

While the electrolytic reduction of technetium is preferred, reduction can also be accomplished using chemical reductants conventionally employed in conjunction with technetium such as $SnCl_2$ or $Na^+BH_4^-$.

It has been found that when tiron is employed as a transfer ligand with reduced technetium, the technetium can easily be maintained in the +5 oxidation state and does not reoxidize when the reducing agent is removed. A technetium-containing transfer complex can be prepared by placing a pertechnetate compound, e.g., $Na^{99m}TcO_4$, and tiron, as the disodium salt, in an aqueous medium in a closed container. The head space in the container is then purged with an inert gas such as argon and the technetium is electrolytically reduced concomitantly with the formation of the transfer complex. Electrolytic reduction can be accomplished by inserting a zirconium electrode into the aqueous medium and passing a sufficient amount of current through the medium to effect reduction, typically about 100 milliamperes for about 2 min. The resultant transfer complex can be used to label a chelate-derivatized protein with technetium in the +5 oxidation state.

The method of the invention results in highly efficient and selective labeling of the protein at the site of the exogenous chelating group. Tiron will not transfer the metal ion to the weaker endogenous chelating groups on the protein.

The examples which follow are intended to illustrate further the practice of the invention and are not intended to limit its scope in any way. Materials used in the Examples were prepared as follows.

Conjugate of Anti-CEA Fab' and [((7maleimidoheptyl)imino)bis(ethylenenitrilo)tetraacetic acid. Murine anti-CEA monoclonal antibody was purified from ascitic fluid by $(NH_4)_2SO_4$ precipitation and ion-exchange chromatography. Enzymatic fragmentation of intact antibody to yield $F(ab')_2$ was accomplished by using thiol-free pre-activated papain according to Parham, et al., *J. Immunol. Methods,* 53:133-173 (1982). Purified $F(ab')_2$ fragment was obtained by sequential column chromatography over Whatman DE-52 and Sephadex G-100 resins. Denaturing gel electrophoresis (SDS-PAGE) showed the isolated protein to be greater than 95% pure.

The $F(ab')_2$ fragment generated by papain cleavage of the anti-CEA monoclonal antibody was determined to have one interchain disulfide bond joining the two heavy chains. This determination was made by reducing the $F(ab')_2$ antibody fragment with dithiothreitol (DTT) under mild reducing conditions to rupture the interchain disulfide bonds joining the two heavy chains as well as the interchain disulfide bonds joining the heavy and light chains, while leaving the intrachain disulfide bonds intact. The reduced fragments were then reacted with $^3$H-NEM—which reacts at the free sulfhydryl groups—and run on SDS-polyacrylamide gels, resulting in bands corresponding to heavy and light chains, each having its free sulfhydryl groups tritiated. The gel was protein stained, fluorophore soaked, dried and exposed to x-ray film to determine the relative intensity in the heavy and light chain bands. The fluor-soaked bands were excised and placed in a scintillation counter. Using the counts per minute for the light chain band as a measure of one sulfhydryl group, the heavy chain was found to contain two sulfhydryls, one of which corresponds to the interchain disulfide bond with the light chain. Consequently, the other sulfhydryl corresponds to a single interchain disulfide bond between the heavy chains of the $F(ab')_2$ fragment produced by papain cleavage of the whole CEA antibody.

$F(ab')_2$ fragments of monoclonal anti-CEA generated by papain-cleavage of whole antibody were reduced for 1-2 hours at room temperature in pH of approximately 7.4 buffer, with a final concentration of 5-20 mM DTT.

Reduced anti-CEA Fab' protein produced by the above-described procedure was freed of excess thiol reagent, under $N_2$ atmosphere, by exhaustive buffer exchange into 50 mM MES, 2 mM $Na_2$EDTA, pH 6.5 to 6.8, using diafiltration with a PM10 membrane. An aliquot of the resulting solution was titrated with $^3$H-NEM of known specific activity to determine the number of free SH groups per Fab' molecule generated by the reduction procedure. The remainder was reacted with 10-25 mM of the coupling agent produced by the previously described procedure, i.e., [((7-maleimidoheptyl)imino)bis(ethylenenitrilo)]tetraacetic acid, for 2 to 4 hours at room temperature, then overnight at 4° C.

EXAMPLE I

Preparation of Chelate Complex of Indium-111 and Anti-CEA Fab' Conjugate Using Tiron as a Transfer Ligand An antibody-radionuclide conjugate was prepared by adding 10 μl of $^{111}$InCl$_3$ (approximately 50 to 100 μCi) in 50 mM HCl (Rad-Pharm) to 5 μl of 10 mM tiron, 4 mM HCl, pH 2.4, and incubating for 5 minutes at room temperature. There were then added 10 μl of 200 mM MES, pH 6.0, and 10 μl of 2-15 mg/ml of the conjugate of anti-CEA Fab' and chelate coupling agent produced by the previously described procedure. The final pH was between 5.0 and 5.5. The reaction mixture was incubated for 1 hour at room temperature, after which 2-5 μl were spotted onto a cellulose acetate strip for electrophoretic analysis. Electrophoresis was conducted using 50 mM Hepes, pH 7.0, as an electrode buffer. In the electrophoretic field, the $^{111}$In-chelated anti-CEA Fab' conjugate remained at the origin and unreacted indium-111 migrated as a separate peak. In a separate electrophoresis, 7 μl of the chelate-conjugate reaction mixture were first incubated with 2 μl of 200 mM Na$_2$EDTA, pH 6.0, prior to electrophoresis. Addition of the EDTA caused a shift in the unreacted tiron-indium-III peak but did not affect the chelate-conjugate peak, indicating that the chelated antibody conjugate was more stable than the $^{111}$In-Tiron chelate. A composite of these results is presented in FIG. 1.

The anti-CEA Fab'/indium-111 conjugate can be administered intravenously in the form of a physiologically acceptable buffered solution for use as a tumor-imaging agent, for example, for imaging tumors of the colon using known photoscanning techniques.

EXAMPLE II

Preparation of Chelate Complex of Gallium-67 and Anti-CEA Fab' Conjugate Using Tiron as a Transfer Ligand 10 μl of Ga-67 (10 mCi/ml in 50 mM HCl) was mixed with 5 μl of 10 mM tiron in each of six metal-free microfuge tubes. The pH of the mixture was buffered with 10 μl of 200 mM MES buffer, pH 6.0. To the three tubes there were then added either (a) 10 μl of 50 mM MES buffer, pH 6.0, (b) 10 μl of 7.7 mg/ml of whole anti-CEA monoclonal antibody or (c) 10 μl of 6 mg of anti-CEA Fab' covalently bound to [5-maleimidopentyl(ethylenedinitrilo)]tetraacetic acid. The contents of the tubes were incubated at room temperature for 1 hour. After the incubation period, 7 μl were removed from each tube and incubated with 2 μl of 0.2 M ethylenediaminetetraacetic acid at room temperature for 30 minutes. The samples were then analyzed by cellulose acetate electrophoresis as described in Example I.

The migration patterns upon electrophoresis indicated that the Ga-67 was transferred by the tiron to the anti-CEA Fab' containing the covalently bound chelating group. Moreover, the Ga-67 which was bound to the anti-CEA Fab' in this manner was not extracted by EDTA. By comparison, the electrophoresis patterns indicated that Ga-67 was extracted by EDTA from the tiron/Ga-67 transfer complex; no Ga-67 was transferred to whole antibody (without the covalently linked chelating group) which had been incubated with tiron/Ga-67.

EXAMPLE III

Use of Tiron as a Transfer Ligand for Technetium-99m

The use of tiron as a transfer ligand for Tc-99m was compared with the use of carboxylated sugars, i.e., glucoheptonate, gluconate and saccharate. Carboxylated sugars have been the most commonly employed transfer ligands for Tc-99m. Three parameters were examined: the ability of the transfer ligand to trap technetium as a single, homogeneous complex, the stability of the transfer complex versus time of incubation and the transferability of technetium from the ligand to a chelate substituted antibody.

Table 1 demonstrates the ability of several carboxylated sugars and tiron to trap technetium in a transferable oxidation state during electrolytic reduction. Electrolytic reduction reaction vials contained 50 mg each of a respective test ligand, 1 ml of water adjusted to pH 7.0 with saturated sodium bicarbonate, and 1 ml of pertechnetate from a technetium generator. The vials were sealed and purged with argon for 5 min. Two zirconium electrodes (2.0 mm diameter) were inserted into the vial, the vial inverted, and a current of 100 mA at 10 volts was passed through the solution for 2 min. The formation of Tc-99m-ligand complex was monitored using ascending paper chromatography in acetonitrile, water (60:40) followed by radiochromatogram scanning. Each of the three carboxylated sugars failed to prevent continued reduction of technetium so that between 24 to 30% of the radioactivity appeared in the $TcO_2$ radiochromatogram peak. Tiron trapped 78% of the technetium as a homogeneous peak allowing only 5.3% of the radioactivity to further reduce to $TcO_2$. Continued electrolytic reduction of the tiron-technetium complex did not result in further accumulation of $TcO_2$.

TABLE 1

Relative Efficiency of Various Transfer Ligands to Trap Reduced Technetium

| Ligand | Complex | Reduced-Hydrolyzed | $TcO_4^-$ |
|---|---|---|---|
| Glucoheptonate | 70.0* | 24.3 | 1.2 |
| Gluconate | 62.0 | 29.9 | 1.4 |
| Saccharate | 51.2 | 23.9 | 9.8 |
| Tiron | 78.0 | 5.3 | 4.9 |

*% of total radiochromatogram radioactivity.

Table 2 compares the stability of the technetium complex of tiron or saccharate versus time of incubation. Tc-99m-tiron and Tc-99m-saccharate were prepared as indicated above. Saccharate shows a progressive loss of complexed technetium from 69.8% to 51.1% with concomitant increase in reduced hydrolyzed technetium from 15.9% to 30.4% over the five hour incubation period. The tiron complex shows only minor change over the same time period.

TABLE 2

Relative Stability of Tc-Tiron and Tc-Saccharate versus Time

| Time (hr.) | Complex | $TcO_2$ |
|---|---|---|
| Saccharate | | |
| 0.5 | 69.8% | 15.9% |
| 2.0 | 62.4% | 24.8% |
| 5.0 | 51.1% | 30.4% |
| Tiron | | |
| 0.5 | 78.0% | 5.8% |
| 2.0 | 65.6% | 12.6% |
| 5.0 | 68.5% | 8.9% |

Figure 2:
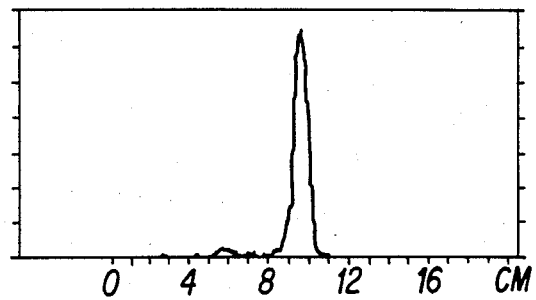
FIG. 2 presents radiochromatograms of: a tiron-$TcO_4$ complex; the same complex after electrolytic reduction; the reaction product of the reduced Tc-tiron complex and an F(ab')$_2$ antibody fragment coupled with a chelating group, $MAG_3$; the reaction product of the reduced Tc-tiron complex and an F(ab')$_2$ antibody fragment coupled with a chelating group, $CO_2DADS$; and the reaction product of the reduced Tc-tiron complex and an acetylated F(ab')$_2$ antibody.
Figure 2:
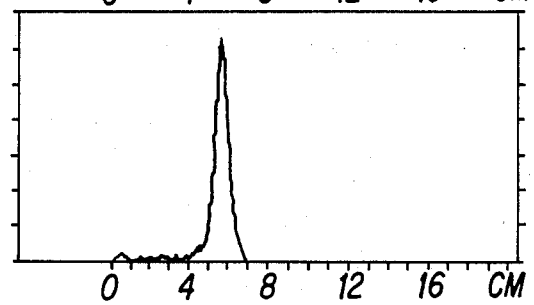
Figure 2:
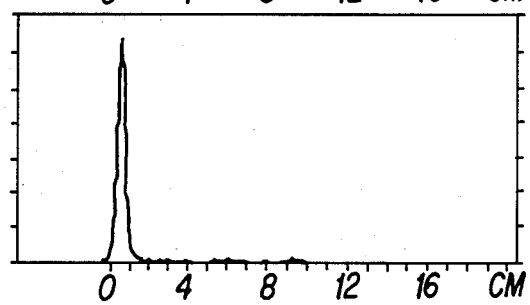
Figure 2:
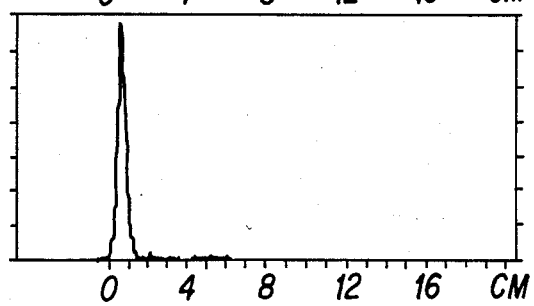
Figure 2:
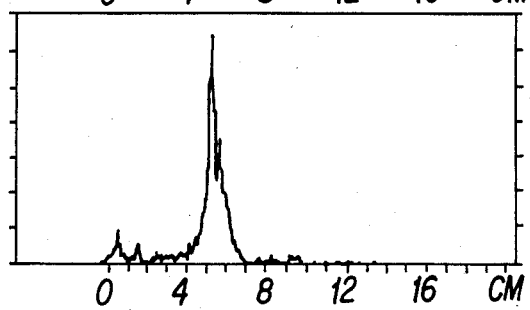

FIG. 2 demonstrates the transferability of technetium from a tiron complex to antibody fragments coupled with either S-acetylmercaptoglycylglycylglycinate (Ac-MAG$_3$) or 2,3 bis(acetylmercaptoacetamido)propionate (Ac-CO$_2$DADS). Electrolytic reduction of pertechnetate in the presence of tiron as indicated above resulted in near quantitative complex formation (89.2%). Challenge of this complex with either Ac-MAG$_3$ or Ac-CO$_2$DADS substituted F(ab')$_2$ fragments resulted in 86.3% and 88.2% of the technetium transferring to the respective antibodies. However, when challenged with acetyl substituted F(ab')$_2$, only 6% of the technetium appeared at the origin of the radiochromatogram. Thus, tirontechnetium complex transfers technetium only to antibodies having strong chelates attached and not to antibodies similarly acylated with non-chelating groups.

What is claimed is:

1. A method of preparing a conjugate of a protein or polypeptide and a metal ion which comprises reacting a metal ion transfer complex comprising a chelate of 4,5-dihydroxyl-m-benzenedisulfonic acid or a salt thereof and a metal ion with a protein or polypeptide that is covalently bound to an exogenous chelating group, said exogenous chelating group having a greater chelating affinity than 4,5-dihydroxyl-m-benzenedisulfonic acid for the metal ion, the reaction being carried out in an aqueous medium at a pH at which the protein or polypeptide is stable.

2. A method as claimed in claim 1, wherein the protein or polypeptide is an antibody or fragment thereof.

3. A method as claimed in claim 1, wherein the protein or polypeptide is an antibody or fragment thereof to a tumor-associated antigen.

4. A method as claimed in claim 1, wherein the protein or polypeptide is an antibody or fragment thereof to carcinoembryonic antigen.

5. A method as claimed in claim 1, wherein the metal ion is selected from the group consisting of Mg, Al, Ca, Sc, Ti, V, Cr, Mn, Fe, Co, Ni, Cu, Zn, Ga, Sr, Y, Zr, Mo, Tc, Pd, Cd, In, Sn, Sb, Ba, Hf, W, Re, Hg, Tl, Rh, Pb, Bi, La, Ce, Pr, Nd, Sm, Eu, Gd, Tb, Dy, Ho, Er, Tm, Yb, Th, U and Pu and isotopes thereof.

6. A method as claimed in claim 1, wherein the metal ion is selected from the group consisting of indium, gallium, technetium and isotopes thereof.

7. A method of preparing a conjugate of a protein or polypeptide and a technetium ion which comprises:
 (a) reacting 4,5-dihydroxyl-m-benzenedisulfonic acid and pertechnetate ions in an aqueous reaction medium;
 (b) electrolytically reducing the pertechnetate ions in the reaction medium of step (a) to an oxidation state less than +7; and
 (c) reacting the chelate of reduced technetium produced in steps (a) and (b) with a protein or polypeptide that is covalently bound to an exogenous chelating group, said exogenous chelating group having a greater chelating affinity than 4,5-dihydroxyl-m-benzenedisulfonic acid for the technetium ion, the reaction being carried out in an aqueous medium at a pH at which the protein or polypeptide is stable.

8. A method as claimed in claim 7, wherein the technetium ion is Tc-99m.

9. A method as claimed in claim 2, 3 or 4, wherein the metal ion is selected from the group consisting of In-111, Ga-67 and Tc-99m.

10. A method as claimed in claim 2, 3 or 4, wherein the protein or polypeptide is an antibody or fragment thereof which has been covalently joined to an exogenous chelating group by reacting it with a coupling agent of the formula

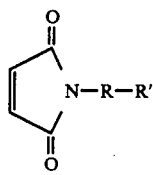
(I)

wherein R is a divalent organic radical and R' is a chelating group.

11. A method as claimed in claim 1, wherein the protein or polypeptide has been covalently joined to an exogenous chelating agent by reacting it with a coupling agent selected from the group consisting of

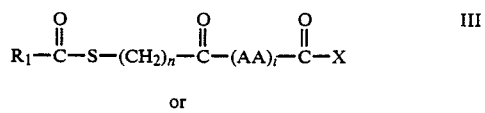

or

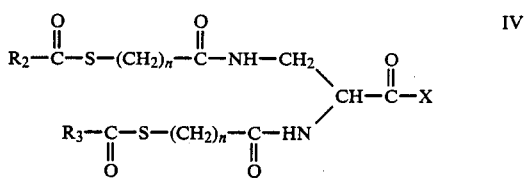

wherein $R_1$, $R_2$ and $R_3$ are the same or different and each represents a radical selected from the group consisting of alkyls having from 1 to 6 carbon atoms, aryls having from 6 to 8 carbon atoms and aralkyls having from 7 to 9 carbon atoms, any of which can be substituted with one or more hydroxyl, alkoxy, carboxy or sulfonate groups; n is either 1 or 2; AA are independently $\alpha$ or $\beta$ amino acid residues linked to each other by amide bonds; i is an integer of from 2 to 6; and X is an activating group capable of forming an amide bond with an $\epsilon$-amino group or an amino terminus of the protein or polypeptide.

* * * * *